(12) United States Patent
Weijand et al.

(10) Patent No.: US 6,470,212 B1
(45) Date of Patent: Oct. 22, 2002

(54) BODY HEAT POWERED IMPLANTABLE MEDICAL DEVICE

(75) Inventors: Koen J. Weijand, Rockanje (NL); Patrick J. Combs, Phoenix, AZ (US); Daniel R. Greeninger, Coon Rapids, MN (US); Richard P. M. Houben, Berg en Terbljit (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/529,292

(22) PCT Filed: Aug. 11, 1999

(86) PCT No.: PCT/US99/18260
§ 371 (c)(1),
(2), (4) Date: Apr. 11, 2000

(87) PCT Pub. No.: WO00/09201
PCT Pub. Date: Feb. 24, 2000

Related U.S. Application Data
(60) Provisional application No. 60/096,080, filed on Aug. 11, 1998.

(51) Int. Cl.$^7$ .................................................. A61N 1/08
(52) U.S. Cl. ........................................... 607/35; 607/61
(58) Field of Search ................................ 607/1, 33, 35, 607/61

(56) References Cited

U.S. PATENT DOCUMENTS

| | | | |
|---|---|---|---|
| 3,649,367 A | 3/1972 | Purdy ........................ 136/202 |
| 3,818,304 A | 6/1974 | Hursen et al. ................. 321/2 |
| 4,316,472 A | 2/1982 | Mirowski et al. | |
| 4,375,817 A | 3/1983 | Engle et al. | |
| 4,379,459 A | 4/1983 | Stein | |
| 4,384,585 A | 5/1983 | Zipes | |
| 4,432,363 A | * 2/1984 | Kakegawa | |
| 4,476,868 A | 10/1984 | Thompson | |
| 4,556,063 A | 12/1985 | Thompson | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,800,883 A | 1/1989 | Winstrom | |
| 4,821,723 A | 4/1989 | Baker, Jr. et al. | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |

(List continued on next page.)

FOREIGN PATENT DOCUMENTS

| | | | | |
|---|---|---|---|---|
| EP | 0533917 | 1/1997 | ............ | O61N/1/39 |
| WO | 9218198 | 10/1992 | ............ | A61N/1/05 |

OTHER PUBLICATIONS

Arzbaecher, Robert et al., "Automatic Tachycardia Recognition", *Pace*, vol. 7, May–Jun. 1984, Part II, pp. 541–547.

Olson, Walter H., et al., "Onset and Stability for Ventricular Tachyarrhythmia Detection in an Implantable Pacer–Cardioverter–Defibrillator", in *Computers in Cardiology*, Oct. 7–10, 1986. Boston MA, IEEE Computer Society Press, pp. 167–170.

*Primary Examiner*—Jeffrey R. Jastrzab
(74) *Attorney, Agent, or Firm*—Girma Wolde-Michael

(57) ABSTRACT

A system for and method of providing power to an implanted medical device within a patient is disclosed. The system (250) includes a first (262) and a second heat conduit (264) positioned within the patient. A thermoelectric device (252) is connected to the first and second heat conduits for thermally converting the temperature difference between the conduits to a voltage. A DC-DC converter (254) is connected to the thermoelectric element and increases the voltage. A storage element (256) is connected to the DC-DC converter- for receiving the increased voltage. The storage element is also connected to the implanted medical device (258), thereby providing power to the implanted medical device.

33 Claims, 12 Drawing Sheets

U.S. PATENT DOCUMENTS

| | | |
|---|---|---|
| 5,099,838 A | 3/1992 | Bardy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,269,198 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,545,186 A | 8/1996 | Olson et al. |
| 5,690,686 A | 11/1997 | Min et al. |
| 5,800,465 A | 9/1998 | Thompson et al. |
| 5,835,457 A | 11/1998 | Nakajima |
| 5,889,735 A | 3/1999 | Kawata et al. |
| 5,891,180 A | 4/1999 | Greeninger et al. |
| 5,897,330 A | 4/1999 | Watanabe et al. |

* cited by examiner

BODY HEAT POWERED IMPLANTABLE MEDICAL DEVICE

This application is a 371 of PCT/US 99/18260 filed Aug. 11, 1999 and claims benefit of Ser. No. 60/096,080 filed Aug. 11, 1998.

FIELD OF THE INVENTION

The present invention relates generally to a system and method used in conjunction with an implantable medical device. More specifically, the present inventing relates to powering an implantable medical device through use of a difference in temperature between locations within a patient.

BACKGROUND OF THE INVENTION

Implantable medical device systems known in the art comprise several components, including an implantable medical device, such as a pacemaker or defibrillator, pacing and/or sensing leads, and a programmer. The leads connect the implantable medical device to the heart of a patient.

An implantable medical device, such as a pacemaker or a defibrillator, is a microprocessor-based component and commonly stores a variety of different types of diagnostic data which assists a clinician or a physician in evaluating both the operation of the patients heart and the operation of the implanted medical device. The specific diagnostic data is stored by the implantable medical device within the microprocessor and includes a variety of information, including a real-time event recording of pacing events. An implantable medical device includes numerous electrical components which must be powered by a power source.

The programmer of the implantable medical device system is located outside of the patient, such as at a hospital or clinic. The programmer can be connected to the implantable medical device via radio frequency (RF) connections. The programmer provides multiple functions, including (a) assessing lead performance during a pacemaker or defibrillator implantation, (b) programming the implantable medical device, and (c) receiving feedback information from the implantable medical device for use by the operator.

An analyzer, which is sometimes a sub-component of the programmer and sometimes an individual component is a microprocessor-base component designed to assess the electrical performance of a pacing lead system used in conjunction with an implantable medical device system. The analyzer utilizes the programmer as a control and display platform.

Pacemakers and defibrillators utilize an internal power supply, such as a battery, to generally power the device, and to specifically power individual electrical components of the device. Prior art batteries of a pacemaker or defibrillator have a fixed life span. For example, most present-day power sources of implantable medical devices have a life span in the range of 4 to 8 years. There is, therefore, a need for a power source used in conjunction with an implantable medical device which will exceed the life span of prior art power sources.

Thermoelectricity is a term that describes the electricity generated by applying heat to the junction of two different materials, such as metals or semiconductors. If two wires of different materials are joined at their ends, and one end is at a higher temperature than the other, a voltage difference will arise, and an electrical current will flow. The voltage difference varies in direct proportion to the temperature difference. This proportionality is used in a device called a thermocouple. Using semiconductor materials instead of metals can increase the current within the thermocouple. In addition, using multiple thermocouples in series can increase voltage.

It is known within the medical industry that there is a temperature difference between a human body and its external surroundings. Recent technology has utilized this temperature difference in order to provide power to electrical and electromechanical components of a device, such as a wristwatch, through use of a thermocouple effect. The patents listed below in Table 1 discuss the concept of utilizing a temperature difference between a human body and its surroundings to generate a voltage which can thereby be used to power a device such as a wrist watch.

| Patent No. | Assignee | Title | Patent Date |
| --- | --- | --- | --- |
| 5,835,457 | Citizen Watch Co., LTD | ELECTRONIC WATCH AND METHOD OF CHARGING THE SAME | November 10, 1998 |
| 5,889,735 | Seiko Instruments, Inc. | THERMO-ELECTRICALLY POWERED WRITSTWATCH | March 30, 1999 |
| 5,897,330 | Citizen Watch Co., LTD | METHOD OF MANU-FACTURING THERMO-ELECTRIC POWER GENERATION | April 27, 1999 |

Similar to the recognition of the difference in temperature between a human body and its surroundings, is the recognition that there are differences in temperatures within a human body. For example, there can be up to a 2° C. temperature difference between internal organs or passageways and their surroundings. It is, therefore, desirous to utilize the temperature difference within a human body to power an implantable medical device, such as a pacemaker, a defibrillator, or any other medical devices discussed in U.S. Pat. No. 5,891,180 to Greeninger et al, hereby incorporated by reference.

SUMMARY OF THE INVENTION

The present invention overcomes the disadvantages of the prior art by providing a method of and a system for supplying power to an implantable medical device within a patient via temperature differentials within the patient.

The present invention has certain objects. That is, the present invention provides solutions to certain problems existing in the prior art such as: (a) an inability to utilize a temperature differential between two leads within a body to provide power to an implantable medical device; (b) an inability to utilize a temperature differential between a first lead position within a lung of a patient and a second lead positioned outside the lung of the patient to provide power to an implantable medical device; (c) an inability to utilize a temperature differential between a first lead positioned within a liver of a patient and a second lead positioned outside the liver of the patient to provide power to an implantable medical device; (d) an inability to utilize a temperature differential between a first lead position within a blood passageway of the body and a second lead positioned outside of the blood passageway to provide power to an implantable medical device; (e) an inability to provide voltage to a storage element, such as a battery or a capacitor, thereby producing a power source for an implantable medical device; (f) an inability to utilize a thermal device and a DC-DC converter to generate a voltage capable of powering an implantable medical device; and (g) an inability to provide the necessary power to an implantable medical device, regardless of a temperature differential between two leads positioned within the patient.

A system and method of the present invention provides certain advantages including: (a) the ability to utilize a temperature differential between two leads within a body to provide power to an implantable medical device; (b) the ability to utilize a temperature differential between a first lead position within a lung of a patient and a second lead positioned outside the lung of the patient to provide power to an implantable medical device; (c) the ability to utilize a temperature differential between a first lead positioned within a liver of a patient and a second lead positioned outside the liver of the patient to provide power to an implantable medical device; (d) the ability to utilize a temperature differential between a first lead position within a blood passageway of the body and a second lead positioned outside of the blood passageway to provide power to an implantable medical device; (e) the ability to provide voltage to a storage element, such as a battery or a capacitor, thereby producing a power source for an implantable medical device; (f) the ability to utilize a thermal device and a DC-DC converter to generate a voltage capable of powering an implantable medical device; and (g) the ability to provide the necessary power to an implantable medical device, regardless of a temperature differential between two leads positioned within the patient.

The system and method of the present invention has certain features, including a first and a second thermocouple lead for positioning within a patient in order to generate a voltage based upon a temperature difference between the two leads. The first and second thermocouple lead of the present invention can be positioned within the patient at numerous locations, as long as there is a temperature differential between the two leads. The temperature difference serves as an input into a thermoelectric device. The thermoelectric device converts the temperature differential between the first and second thermocouple leads to a voltage. Another feature of the present invention is a DC-DC converted connected to the thermoelectric element for increasing the voltage by producing an increased voltage. A further feature of the present invention of the present invention is a storage element connected to the DC-to-DC converter for receiving the increased voltage. The storage element is also connected to the implantable medical device, thereby providing power to the implantable medical device. The storage element is capable of receiving and maintaining an excess amount of electrical energy such that the storage element can provide continuous power to the implantable medical device even in the absence of a temperature differential between the first and second thermocouple leads. Conversely, another feature of the present invention is the ability to supplement a separate, primary power system.

Other objects, advantages, and features of the invention will become apparent by referring to the appended drawings, detailed description, and claims.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
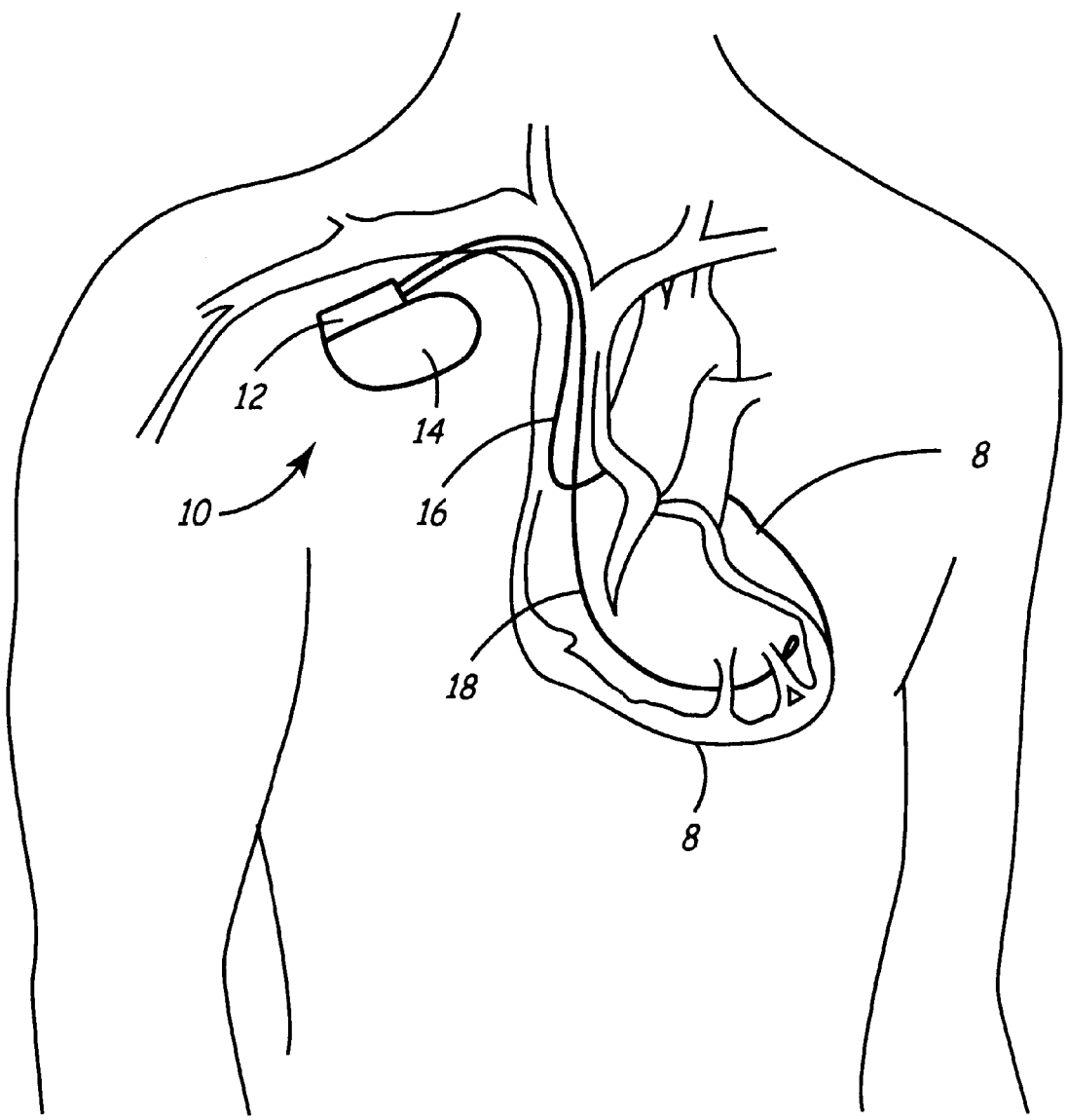
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
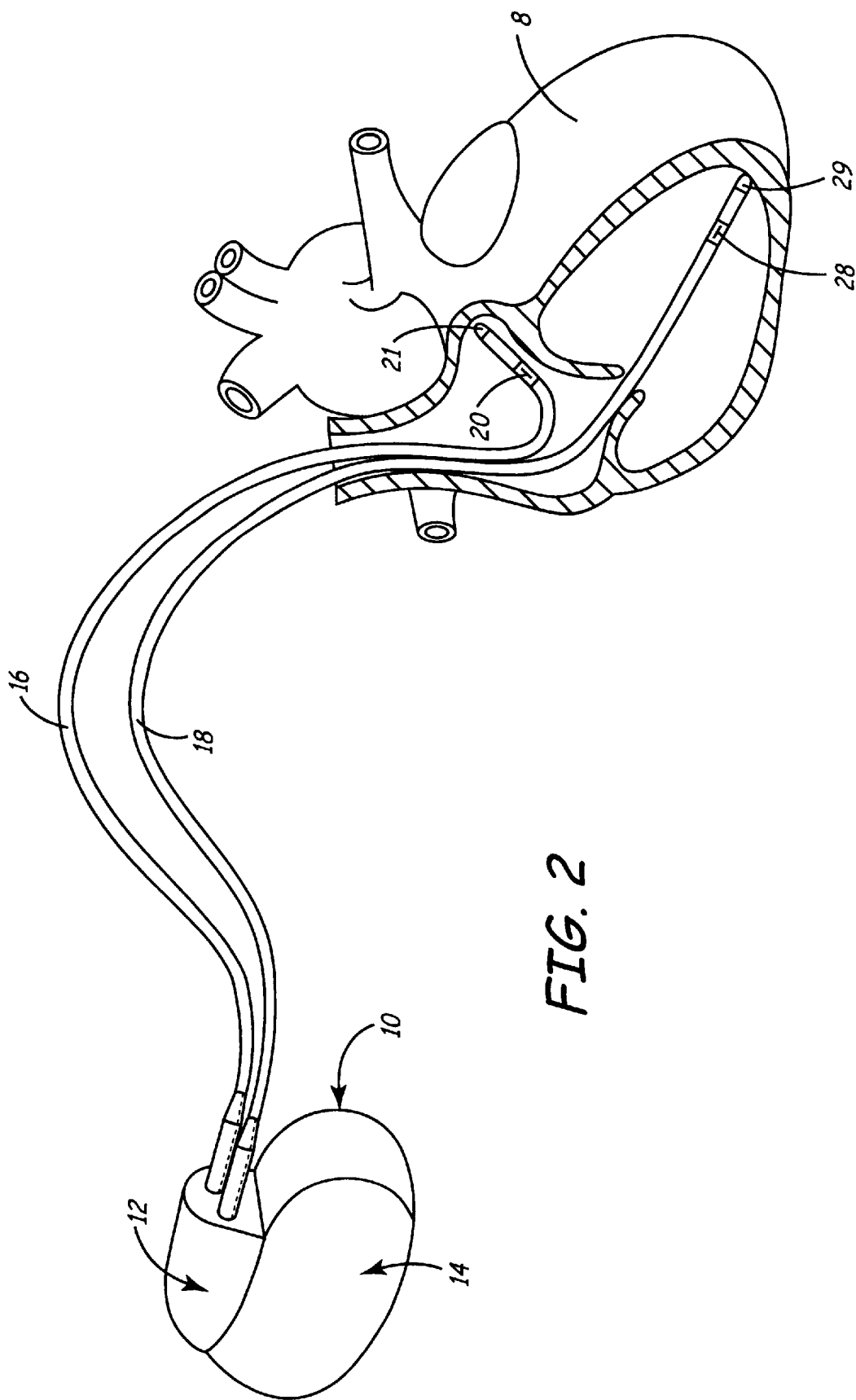
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
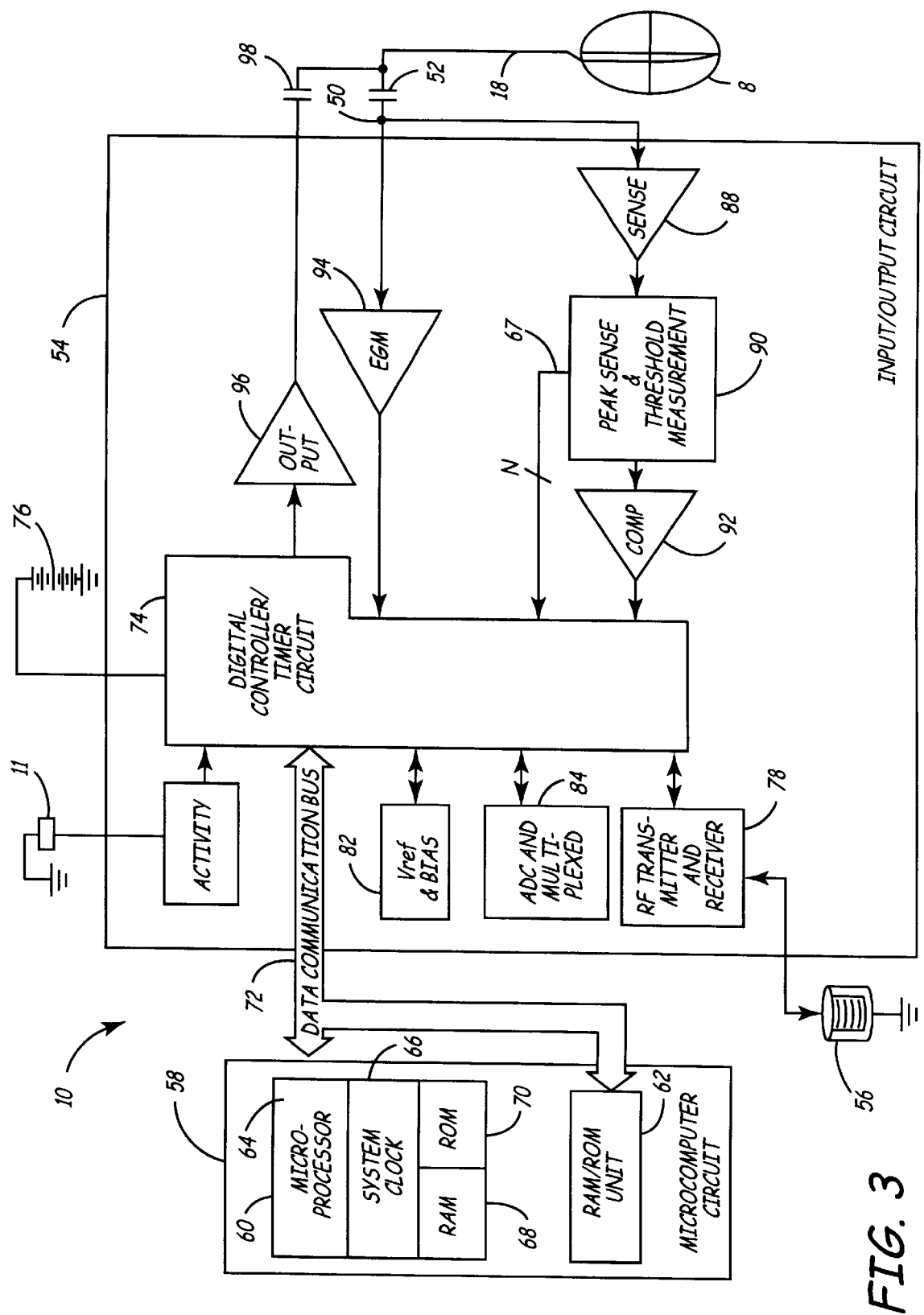
FIG. 3 is a block diagram illustrating the constituent components of an implantable medical device.

FIG. 3 shows a block diagram illustrating the constituent components of IMD in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

Figure 6:
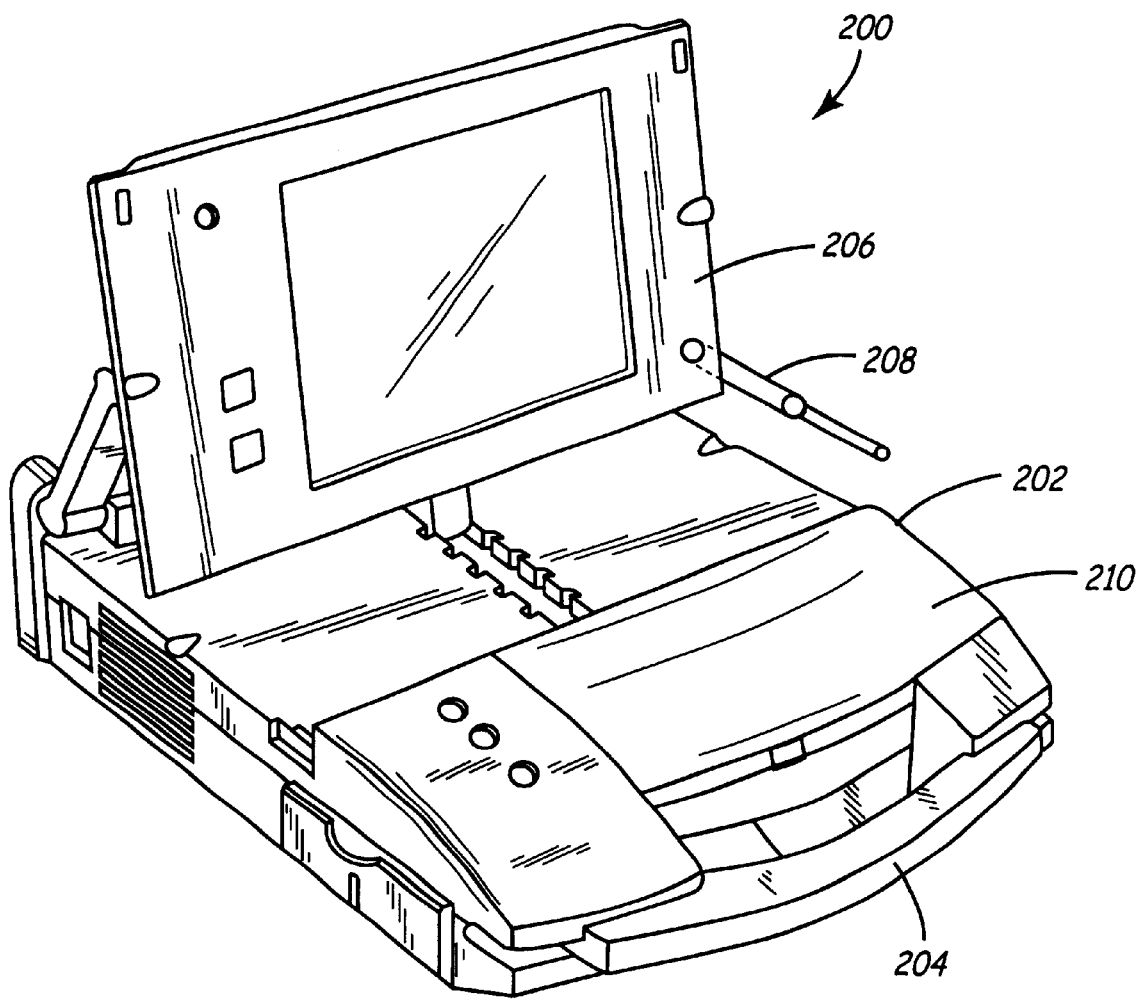
FIG. 6 is a perspective view of a programmer unit used in conjunction with an implantable medical device.

IMD 10 in FIG. 3 is most preferably programmable by means of an external programming unit (shown in FIG. 6). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the EWD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, ND 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
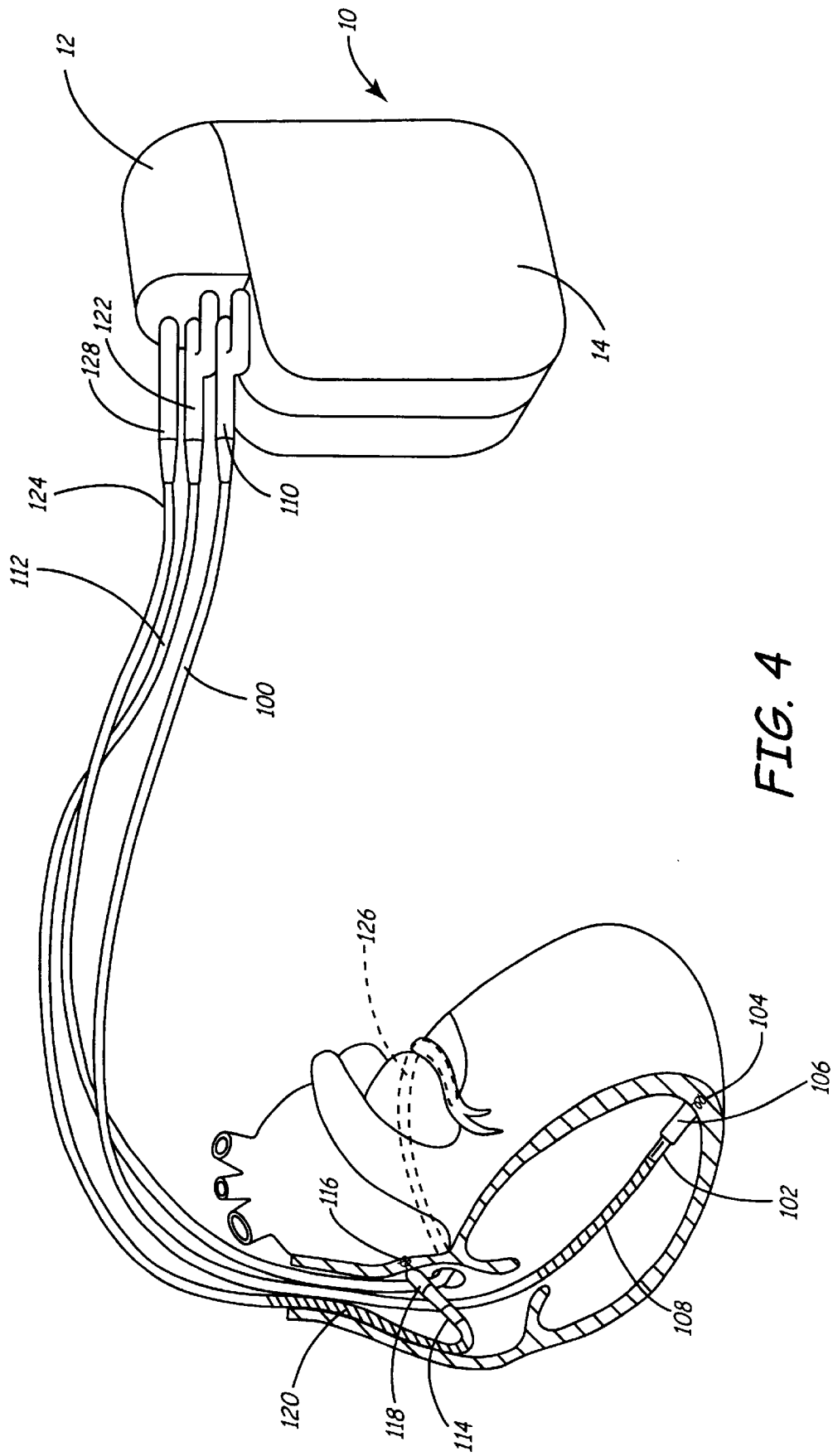
FIG. 4 is a simplified schematic view of an implantable medical device with leads positioned within passageways of a heart.
Figure 5:
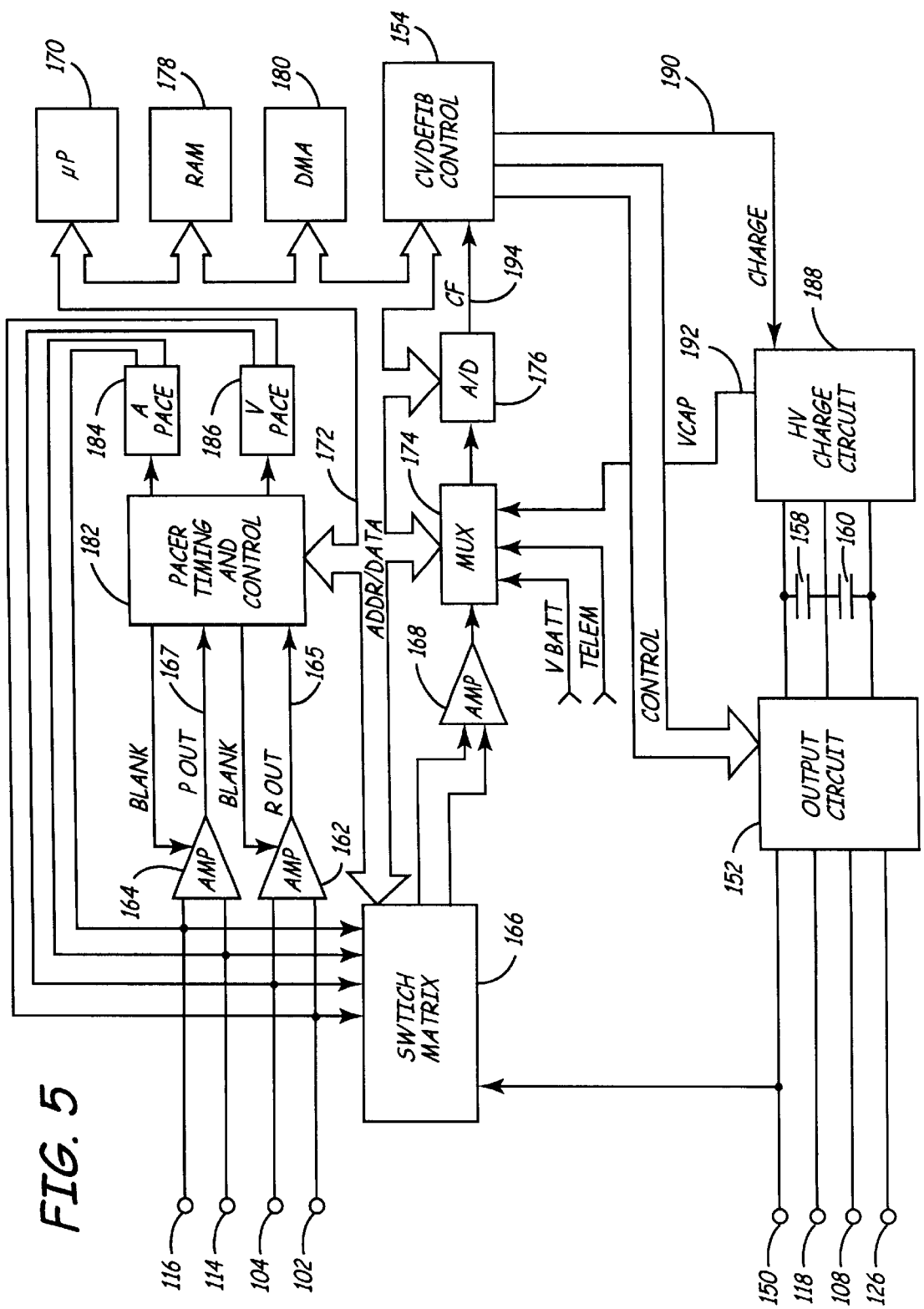
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 100 carrying three concentric coiled conductors separated from one another by tubular insulative sheaths. Located adjacent the distal end of lead 100 are ring electrode 102, extendable helix electrode 104 mounted retractably within insulative electrode head 106 and elongated coil electrode 108. Each of the electrodes is coupled to one of the coiled conductors within lead body 100. Electrodes 102 and 104 are employed for cardiac pacing and for sensing ventricular depolarizations. At the proximal end of the lead is bifurcated connector 110 which carries three electrical connectors, each coupled to one of the coiled conductors. Elongated coil electrode 108, which is a defibrillation electrode 108, may be fabricated from platinum, platinum alloy or other materials known to be usable in implantable defibrillation electrodes and may be about 5 cm in length.

The atrial/SVC lead shown in FIG. 4 includes elongated insulative lead body 112 carrying three concentric coiled conductors separated from one another by tubular insulative sheaths corresponding to the structure of the ventricular lead. Located adjacent the J-shaped distal end of the lead are ring electrode 114 and extendable helix electrode 116 mounted retractably within an insulative electrode head 118. Each of the electrodes is coupled to one of the coiled conductors within lead body 112. Electrodes 114 and 116 are employed for atrial pacing and for sensing atrial depolarizations. Elongated coil electrode 120 is provided proximal to electrode 114 and coupled to the third conductor within lead body 112. Electrode 120 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 122 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 124 carrying one coiled conductor coupled to an elongated coiled defibrillation electrode 126. Electrode 126, illustrated in broken outline in FIG. 4, is located within the coronary sinus and great vein of the heart. At the proximal end of the lead is connector plug 128 carrying an electrical connector coupled to the coiled conductor. Elongated coil defibrillation electrode 126 may be about 5 cm in length.

IMD 10 is shown in FIG. 4 in combination with leads 100, 112 and 124, and lead connector assemblies 110, 122 and 128 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the-electrode configuration of FIG. 4 is employed, the correspondence to the illustrated electrodes is as follows. Electrode 150 in FIG. 5 includes the uninsulated portion of the housing of IMD 10. Electrodes 108, 118, 126 and 150 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of a capacitor bank (which includes capacitors 158 and 160) during delivery of defibrillation pulses.

Electrodes 102 and 104 are located on or in the ventricle of the patient and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium of the patient and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold. The general operation of R-wave and P-wave amplifiers 162 and 164 may correspond to that disclosed in U.S. Pat. No. 5,117,824 to Keimel et al., hereby incorporated by reference herein in its entirety.

Switch matrix 166 is used to select which of the available electrodes are coupled to wide band (0.5–200 Hz) amplifier 168 for use in digital signal analysis. Selection of electrodes is controlled by microprocessor 170 via data/address bus 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 102, 104, 112 and 116. Escape interval counters are also reset on generation of pacing pulses and thereby control the basic timing of cardiac pacing functions, including anti-tachyarrhythmia pacing. The durations of the intervals defined by escape interval timers are determined by microprocessor 170 via data/address bus 172. The value of the count present in the escape interval counters when reset by sensed R-waves and P-waves may be used to measure the durations of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 182 corresponding to the occurrence of sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Serial No. U.S. Ser. No. 92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182 via data bus 172, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 170 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 170 activates cardioversion/defibrillation control circuitry 154, which initiates charging of high voltage capacitors 158 and 160 via charging circuit 188, under the control of high voltage charging control line 190. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion pulse is controlled by pacer timing/control circuitry 182. Following delivery of the fibrillation or tachycardia therapy microprocessor 170 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety.

FIG. 6 is a perspective view of programmer unit 200 used in conjunction with the present invention. Programmer unit 200 has various features, including outer housing 202, carrying. handle 204, articulate display screen 206, stylus 208, and analyzer 210.

Display unit 206 is disposed on the upper surface of housing 202. Display screen 206 folds down in a closed position when programmer 200 is not in use, thereby reducing the size of programmer 200 and protecting the display surface of display screen 206 during transportation and storage. In the perspective view of FIG. 6, programmer 200 is shown with articulate display screen 206 having been lifted up into one of a plurality of possible open positions such that the display area is visible to a user situated in front of programmer 200. Display screen 206 is preferably an LCD or electroluminescent type, characterized by being relatively thin as compared to a cathode ray tube display, or the like. Display screen 206 is operatively coupled to computer circuitry disposed within housing 202 and is adapted to provide a visual display of graphics and/or alphanumeric data under control of the computer circuitry.

Display screen 206 is provided with touch-sensitivity capability, such that a user can interact with the internal computer by touching the display area of display screen 206 with stylus 208. It is believed that those of ordinary skill in the computer will be familiar with touch-sensitivity display technology, and the details of implementation of such display will not be described further herein. Display screen 206 is the primary input medium for programmer 200, and therefore preferably has sufficient resolution to support operations including selection, gestures, annotation, and character recognition.

Analyzer 210, which in prior art devices was a separate unit capable of connection to programmer unit 200 only via connecting cables, provides a medium for an operator to run a series of diagnostic tests during an implantation procedure of an IMD, such as IMD 10 previously discussed. For example, a continuous-time waveform or a single complex waveform can be analyzed by analyzer 210 and displayed on display screen 206 from a variety of implanted leads, such as a lead positioned in an atrium or ventricle of heart 8 (shown in FIGS. 1, 2, 3, and 4).

Figure 7:
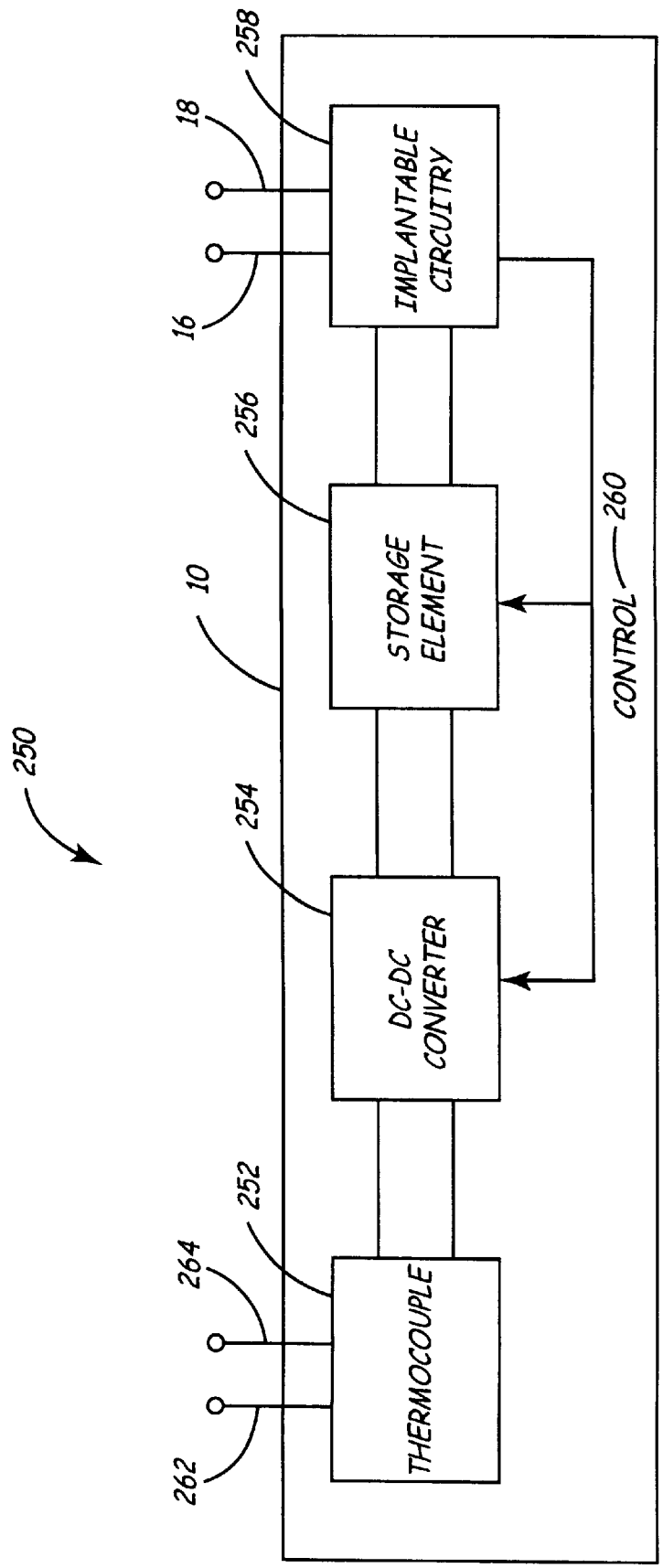
FIG. 7 is a block diagram illustrating the elements of the present invention.

FIG. 7 is a block diagram illustrating the elements of the present invention. As shown in FIG. 7, system 250 includes IMD 10, which further includes pacing and sensing leads 16 and 18, thermocouple 252, DC-DC converter 254, storage element 256, implantable circuitry 258, control 260 and thermocouple leads 262 and 264. IMD 10 is positioned within a patient. IMD 10 represents various implantable medical devices, such as cardiac pacemakers, defibrillators, pacemaker/defibrillator combinations, drug delivery systems, electrical stimulators including nerve and muscle stimulators, deep brain stimulators, or heart assist devices or pumps.

System 250, shown in FIG. 7, illustrates the present invention. Thermocouple leads 262 and 264 are heat conduits positioned within the patient at specific locations such that there is a temperature differential between thermocouple leads 262 and 264. Any location of thermocouple leads 262 and 264 within a patient is acceptable, as long as a temperature difference between the leads is established. Various organs, muscles, and passageways have different and varying temperatures. For example, an organ such as the liver is-at an elevated temperature with respect to its surroundings. Similarly, the passageway to a lung or bronchia is usually at a temperature cooler than its surroundings. Another example of a temperature differential is a temperature of blood flowing through a passageway, such as an artery or vein, with respect to its surroundings. The temperature of the blood, due to its constant motion, is normally at an elevated temperature with respect to its surroundings. In order to ensure a temperature differential, one of the pair of thermocouple leads 262 and 264 is positioned within an organ, muscle, or passageway, such as the liver, the passageway of the lungs/bronchia, or a blood passageway, while the second lead of the pair of thermocouple leads 262 and 264 is positioned at a different location. In one preferred embodiment, the second lead would be positioned adjacent to or in direct contact with the outer casing of enclosure 14 of IMD 10.

Thermocouple 252 will receive the temperature differential between thermocouple leads 262 and 264. In one preferred embodiment, the difference in temperature between thermocouple leads 262 and 264 is in a range of approximately 0.1° C.–5.0° C.

As previously discussed, thermoelectricity is a term that describes electricity generated by a difference in temperature at a junction of two conduits, such as metals or semiconductors. If two conduits are joined at their ends, and one conduit is at a higher temperature than the other, a voltage difference will arise and an electrical current will flow. The voltage difference varies in direct proportion to the temperature difference. Thermocouple leads 262 and 264 provide a temperature differential to thermocouple 252. In one preferred embodiment, thermocouple leads 262 and 264 are either thermally insulated wires or heat pipes; a term common to those skilled in the thermoelectric field. In one preferred embodiment, thermocouple 252 registers an electric voltage in the range of approximately 0.1–1000 millivolts in response to the temperature differential between thermocouple leads 262 and 264.

DC-DC converter 254 is a standard component well-known in the art, such as described in U.S. Pat. No. 3,818,304 to Hursen et al. In particular, DC-DC converter 254 is a modern semi-conductor converter using, for example, JFETs to create a voltage level capable of directly or partially powering implantable circuitry 258 and IMD 10. A voltage of less than 5 millivolts is a sufficient input to DC-DC converter. In one preferred embodiment, DC-DC converter 254 will produce a voltage in the range of 1.0–10 volts. This increased voltage can be provided to either storage element 256 or directly to inplantable circuitry 258 of ID 10.

In one preferred embodiment, storage element 256 is a battery, a capacitor, or a super capacitor. The voltage produced by DC-DC converter 254 can be stored within storage element 256. Thus, there may be times in which thermocouple leads 262 and 264 do not register a temperature difference and no voltage will be produced by thermocouple 252. During these periods, the electrical energy stored within storage element 256 can provide power to i plantable circuitry 258 and IMD 10.

Figure 8:
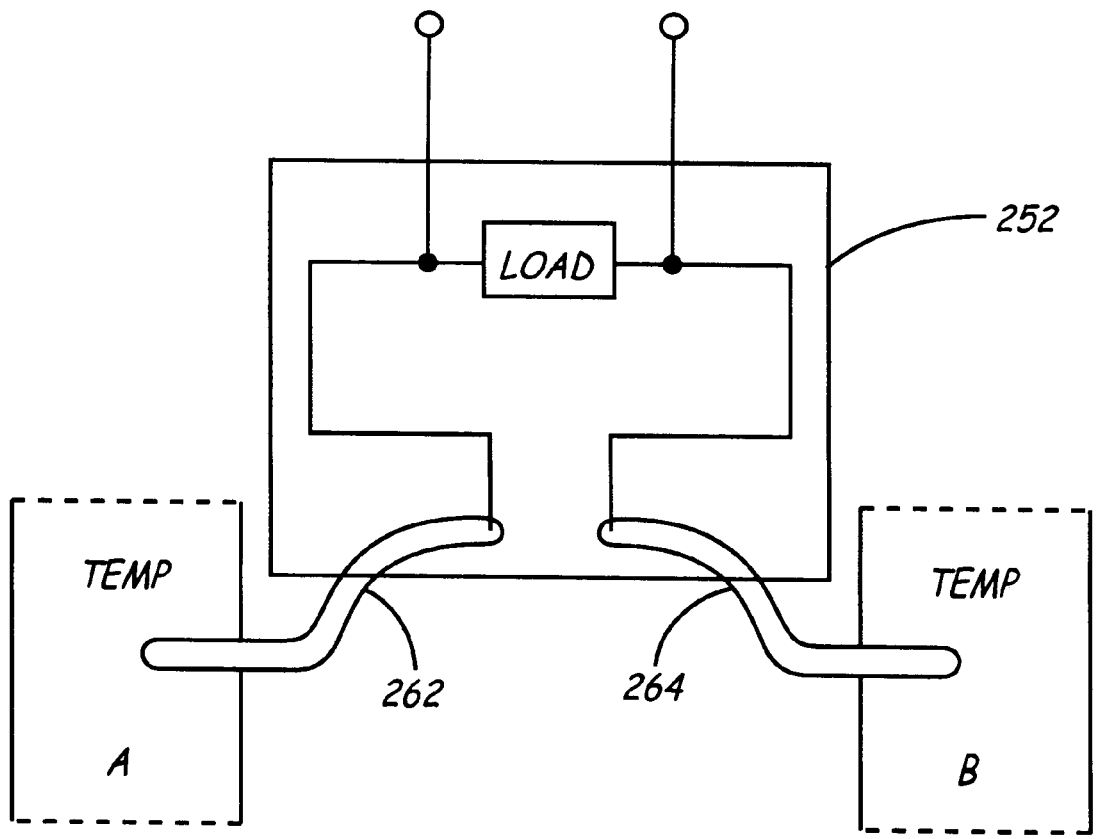
FIG. 8 is a schematic drawing illustrating a basic thermoelectric energy converter used in conjunction with the present invention.

FIG. 8 is a schematic drawing illustrating thermocouple 252. Thermocouple components are known in a medical device art. For example, one type of thermocouple which can be used in conjunction with the present invention is described in U.S. Pat. No. 5,897,330 to Watanabe et al.

As shown in FIG. 8, thermocouple leads 262 and 264 are positioned within the patient at different locations having different temperatures. Particularly, thermocouple lead 262 is positioned with one end positioned within a body part at temperature A, while thermocouple lead 264 is positioned at a second body location at temperature B. For example, thermocouple lead 262 could be positioned within an organ or passageway, such as a liver, a lung passageway, or a blood passageway. Thermocouple lead 262 could also be positioned proximal to the body surface. Conversely, thermocouple lead 264 can be positioned within IMD 10 or attached to the enclosure of IMD 10, or could be positioned outside of IMD 10. It is understood that while a single thermocouple element is shown in FIGS. 7 and 8, multiple thermocouples could be connected in series in. order to provide a greater voltage to DC-DC converter 254, shown in FIG. 7.

Figure 9:
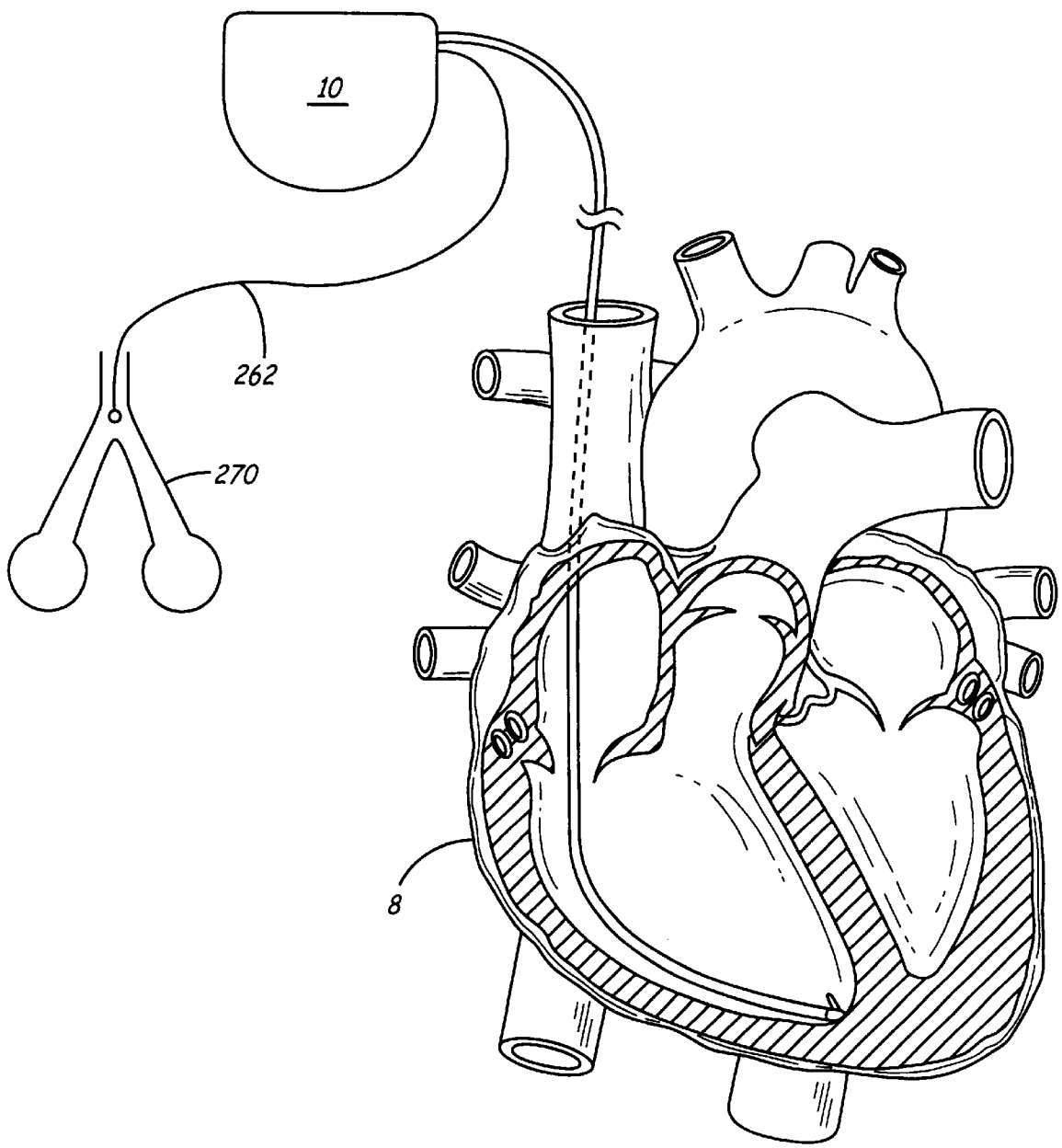
FIG. 9 is a schematic drawing illustrating a first thermoelectric lead position within a lung of a patient and a second thermoelectric lead position adjacent to an implantable medical device used in conjunction with one preferred embodiment of the present invention.

FIG. 9 is a schematic diagram generally illustrating heart 8, IMD 10, and lungs 270. FIG. 9 represents one embodiment of the present invention. As shown in FIG. 9, only thermocouple lead 262 is shown exterior to IMD 10. Thermocouple lead 264, in this embodiment, is positioned within IMD 10. In most circumstances, the passageways of the lungs or bronchia is at a temperature different than the temperature within IMD 10. Thus, a temperature differential is realized between thermocouple lead 262 and 264. This temperature differential creates a voltage within thermocouple 252 which can power IMD 10 via DC-DC converter 254. In most instances, the temperature within lungsibronchia 270 is lower than the temperature within IMD 10. However, there are instances in which the temperature within lungs/bronchia 270 may increase and equal or be greater than the temperature within IMD 10. In this situation, storage element 256, shown in FIG. 7, would provide a power source to IMD 10.

Figure 10:
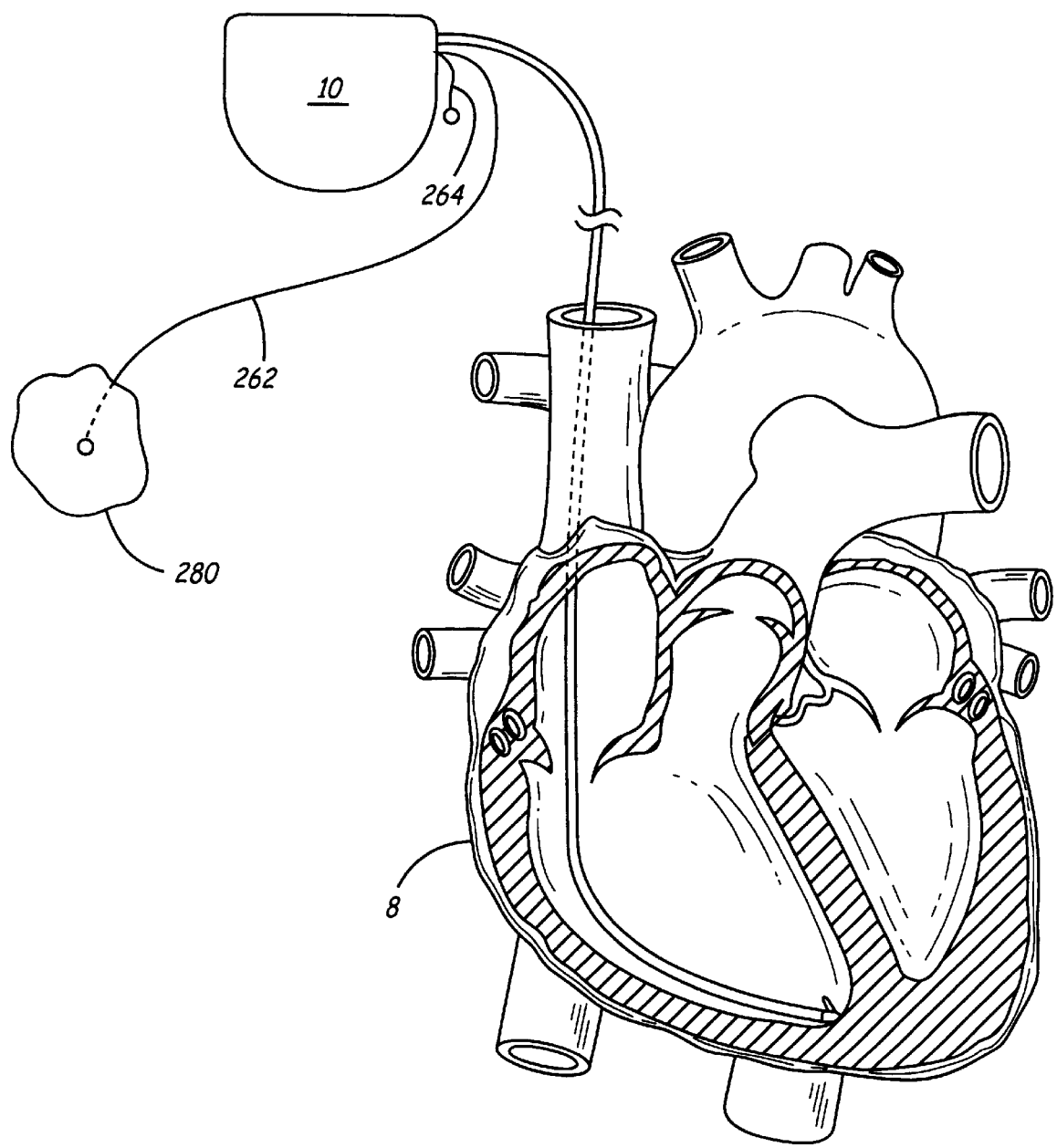
FIG. 10 is a schematic drawing illustrating a first thermoelectric lead positioned within a liver of a patient and a second thermoelectric lead positioned outside of an implantable medical device used in conjunction with another preferred embodiment of the present invention.

FIG. 10 is a schematic diagram illustrating another embodiment of the present invention. FIG. 10 includes heart 8, IMD 10, and liver 280. As shown in FIG. 10, thermocouple lead 262 is positioned within liver 280, while thermocouple 264 is positioned outside of IMD 10, but immediately adjacent IMD 10.

Similar to the example shown in FIG. 9, a temperature difference would be realized between thermocouple 262 within liver 280 and thermocouple lead 264 adjacent IMD 10. It is understood that a liver usually has a temperature of up to 2° C. greater than its surroundings. This temperature differential would produce a voltage within thermocouple 252. The voltage can then be increased by DC-DC converter 254 and provided to IMD 10 as a power source or provided to storage element 256.

Figure 11:
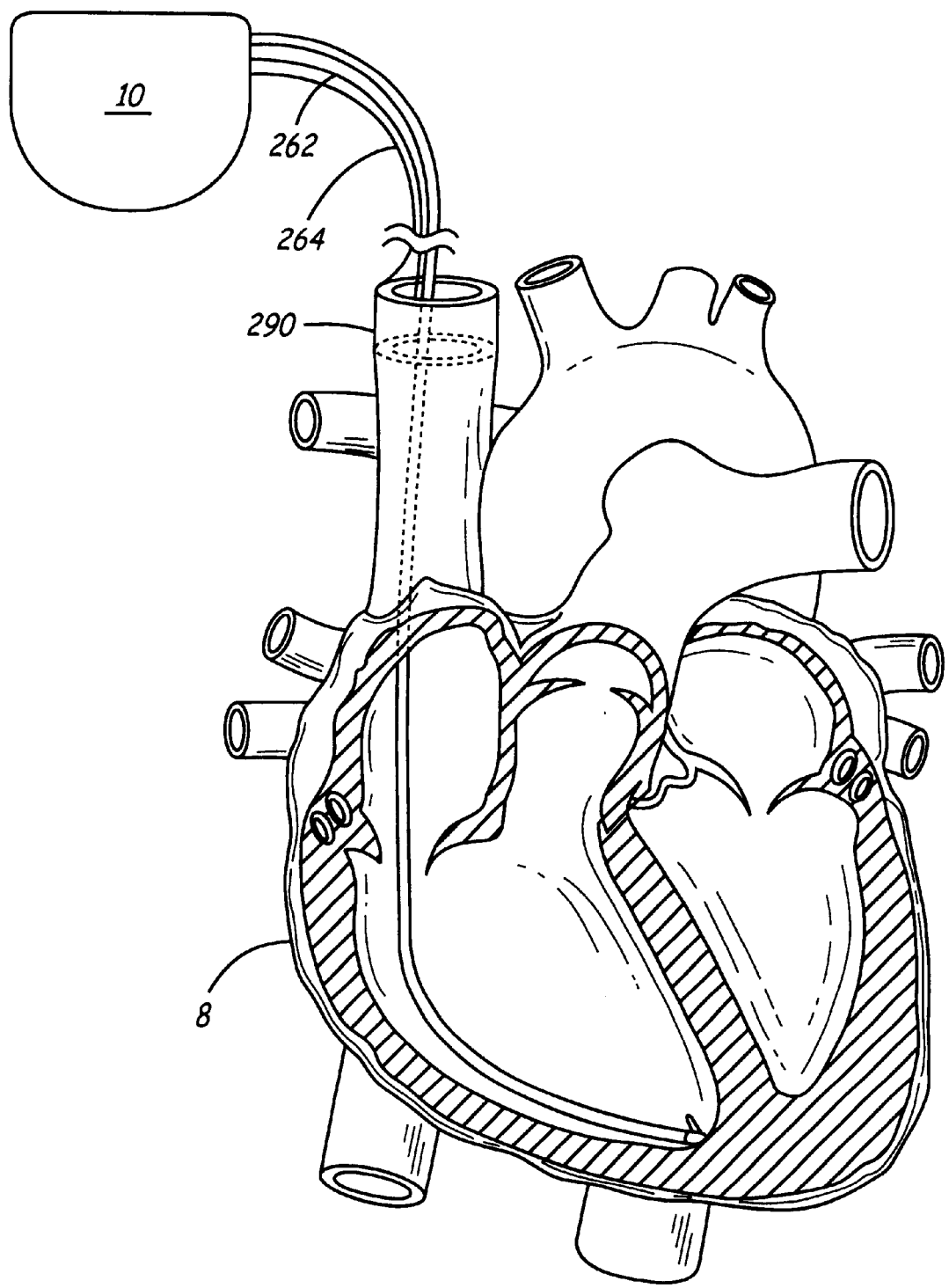
FIG. 11 is a schematic drawing illustrating both thermoelectric leads position within a blood passageway of a patient used in conjunction with yet another preferred embodiment of the present invention.

FIG. 11 is schematic diagram illustrating another embodiment of the present invention. The schematic in FIG. 11 includes heart 8 and IMD 10. In this embodiment, thermocouple leads 262 and 264 are positioned within heart 8. In particular, thermocouple lead 262 is attached to an inner portion of hot and cold junction flow detector 290, while thermocouple lead 264 is attached to the outer surface of hot and cold junction flow detector 290. Hot and cold junction flow detector 290 is positioned about a blood flow passageway.

In this embodiment of the present invention, the temperature of blood traveling through hot and cold flow detector 290 shows small, spontaneous variations due to heat-dependent heat production in the heart and varying activity of skeletal muscles. Hot and cold junction flow detector 290 is positioned in the blood stream and generates a small voltage. This small voltage can be input into DC-DC converter 254 in order to provide electrical energy to IMD 10.

Figure 12:
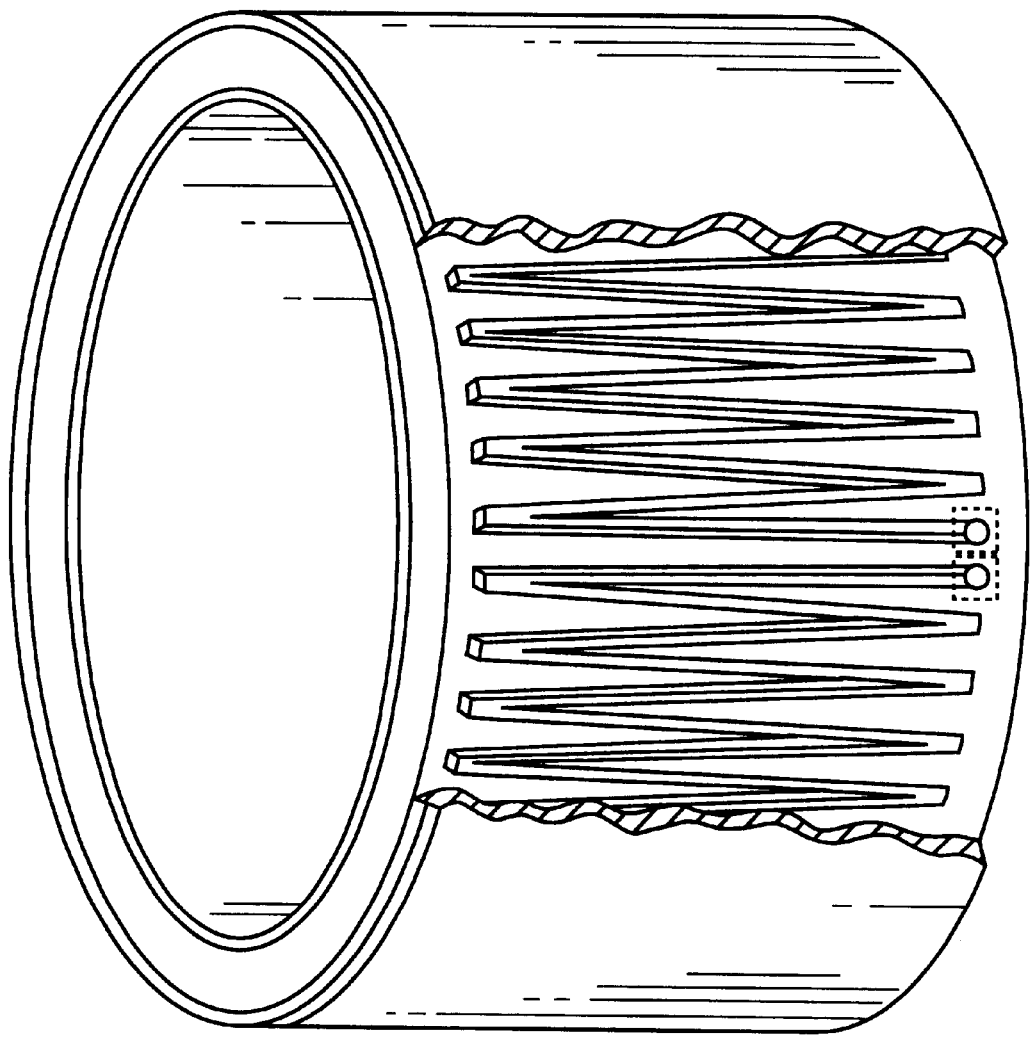
FIG. 12 is a schematic drawing showing a junction flow detector used in conjunction with the preferred embodiment shown in FIG. 11.

FIG. 12 is a schematic diagram illustrating hot and cold junctions flow detector 290. As shown in FIG. 12, hot and cold junction flow detector includes numerous thermocouple elements 292 connected in a series configuration. This series configuration provides a greater voltage within thermocouple 252 which is input into DC-DC converter 254.

With the present invention, a temperature difference between two internal locations of a patient provides the basis for an energy source to power an inplantable medical device. Thus, a specific energy source component having a maximum life capacity is no longer necessary for an inplantable medical device. The temperature differential between two conduits provides an input to a thermocouple element which thereby produces a voltage. The voltage is input into a DC-DC converter in order to provide sufficient energy to power an inplantable medical device. A storage device, such as a battery or capacitor can be utilized to store excess energy which can be used when minimal energy is being harnessed due to a minimal temperature differential between the two conduits.

In the claims section of this application, means-plus-function clauses are intended to cover the structures described herein as performing the recited function and not only structural equivalents but also equivalent structures. For example, although a nail and a screw may not be structurally equivalent in that a nail employs a cylindrical surface to secure wooden parts together, whereas a screw employs a helical surface, in the environment of fastening wood parts, a nail and a screw are equivalent structures.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. An implantable medical device, comprising:
    a sealed enclosure;
    electrical circuitry housed within the sealed enclosure and controlling the delivery of patient therapy;
    an implantable first heat conduit external to the sealed enclosure for sensing a first temperature at a first location within the patient;
    an implantable second heat conduit external to the sealed enclosure for sensing a second temperature at a second location within the patient;
    a thermoelectric device connectable to the first and second implantable heat conduits through a connector module mounted to the sealed enclosure, said thermoelectric device generating a voltage by thermally converting a temperature difference between the first and second implantable heat conduits to an electrical current;
    a DC-DC converter connected to the thermoelectric device, said converter increasing the amplitude of the voltage generated by the thermoelectric device to produce an increased amplitude output voltage; and
    an electrical storage element within the sealed enclosure, the storage element being connected to the .DC-DC converter to receive the increased amplitude output voltage, the storage element also being connected to the electrical circuitry to provide operating power.

2. The device of claim 1, wherein the first heat conduit is implantable within a passageway of a lung of the patient.

3. The device of claim 1, wherein the first heat conduit is implantable within a bronchia of the patient.

4. The device of claim 1, wherein the first heat conduit is implantable within a liver of the patient.

5. The device of claim 1, wherein the first heat conduit is implantable within a blood passageway within the patient.

6. The device of claim 1, wherein the thermoelectric device further comprises a plurality of thermocouples positioned in a series configuration.

7. The device of claim 1, wherein the thermoelectric device converts a temperature difference between the first and second conduits that is in the range of approximately 0.1° C.–5.0° C.

8. The device of claim 1, wherein the thermoelectric device generates a voltage in the range of approximately 0.1–1000 millivolts.

9. The device of claim 1, wherein the DC-DC converter produces a voltage in the range of approximately 1.0–10 volts.

10. The device of claim 1, wherein the storage element comprises a battery.

11. The device of claim 1, wherein the storage element comprises a capacitor.

12. An implantable medical device comprising:
    a sealed enclosure;
    electrical circuitry within the sealed enclosure controlling the delivery of patient therapy;
    first implantable means external to the sealed enclosure for sensing a first temperature;
    second implantable means external to the sealed enclosure for sensing a second temperature;
    means coupled to the first and second implantable temperature sensing means for converting a temperature differential between the first sensed temperature and the second sensed temperature to a voltage;
    means for increasing the amplitude of the converted voltage to an increased amplitude voltage;
    means for storing the increased amplitude voltage; and
    means for providing a portion of the increased amplitude voltage to the electrical circuitry.

13. A method of providing power to an electrical circuit of an implantable medical device controlling the delivery of patient therapy, the method comprising the steps of:
    sensing a first temperature at a first location within the patient external of the device;
    sensing a second temperature at a second location within the patient external of the device;
    converting a temperature difference between the first and second temperatures to a voltage; and
    providing the voltage to power the electrical circuit of the implantable medical device.

14. The method of claim 13, wherein the step of sensing a first temperature further comprises:
    sensing a first temperature within a passageway of a lung of the patient.

15. The method of claim 13, wherein the step of sensing a first temperature further comprises:
    sensing a first temperature within a bronchia of the patient.

16. The method of claim 13, wherein the step of sensing a first temperature further comprises:
    sensing a first temperature within a liver of the patient.

17. The method of claim 13, wherein the step of sensing a first temperature further comprises:
    sensing a first temperature within a blood passageway of the patient.

18. The method of claim 13, wherein the step of sensing a second temperature further comprises:
    sensing a temperature at a location within the patient that is proximate to an outer casing of the implantable medical device.

19. The method of claim 13, wherein the step of converting a temperature difference further comprises:

converting a temperature difference between the first and second temperatures in the range of 0.1° C.–5.0° C. to a voltage.

20. The method of claim 13, wherein the step of converting a temperature difference further comprises:

converting a temperature difference between the first and second temperatures to a voltage in the range of approximately 0.1–1000 millivolts.

21. The method of claim 13, and further comprising: increasing the voltage to an increased voltage in the range of 1.0–10 volts.

22. A method of providing power to an electrical circuit of an implantable medical device controlling the delivery of patient therapy, the method comprising the steps of:

sensing a first temperature at a first location within the patient external of the device;

sensing a second temperature at a second location within the patient external of the device;

converting a temperature difference between the first and second temperatures to a voltage;

increasing the voltage to an increased amplitude voltage;

storing the increased amplitude voltage; and providing a portion of the increased voltage amplitude to the electrical circuit of the implantable device.

23. The method claim 22, wherein the step of sensing a first temperature further comprises:

sensing a first temperature within a passageway of a lung of the patient.

24. The method of claim 22, wherein the step of sensing a first temperature further comprises:

sensing a first temperature within a bronchia of the patient.

25. The method of claim 22, wherein the step of sensing a first temperature further comprises:

sensing a first temperature within a liver of the patient.

26. The method of claim 22, wherein the step of sensing a first temperature further comprises:

sensing a first temperature within a blood passageway of the patient.

27. The method of claim 22, wherein the step of converting a temperature difference further comprises:

converting a temperature difference between the first and second temperatures to a voltage in the range of approximately 0.1–1000 millivolts.

28. The method of claim 22, wherein the step of converting a temperature difference further comprises:

converting a temperature difference between the first and second temperatures in the range of approximately 0.1° C.–5.0° C. to a voltage.

29. The method of claim 22, wherein the step of increasing the voltage further comprises:

increasing the voltage to an increased voltage in the range of 1.0–10.0 volts.

30. The method of claim 22, wherein the step of storing the increased voltage further comprises:

storing the increased voltage within a battery.

31. The method of claim 22, wherein the step of storing the increased voltage further comprises:

storing the increased voltage within a capacitor.

32. The device of claim 1, wherein the first and second implantable heat conduits comprise a semiconducting material.

33. The device of claim 1, wherein the first and second implantable heat conduits comprise thermocouple leads.

* * * * *

UNITED STATES PATENT AND TRADEMARK OFFICE
CERTIFICATE OF CORRECTION

PATENT NO. : 6,470,212 B1
DATED : October 22, 2002
INVENTOR(S) : Koen J. Weijand et al.

It is certified that error appears in the above-identified patent and that said Letters Patent is hereby corrected as shown below:

Title page,
Item [57], ABSTRACT,
Line 1, before "method", insert -- a --.
Line 6, after "between the" insert -- first and second --.
Line 8, after "the voltage" insert -- , thereby providing an increased voltage --.

Column 15,
Line 53, delete ".DC-DC" and insert -- DC-DC --.

Column 16,
Lines 37 and 40, delete "external of the device".

Column 17,
Lines 16 and 18, delete "external of the device".

Signed and Sealed this

Ninth Day of November, 2004

JON W. DUDAS
*Director of the United States Patent and Trademark Office*